United States Patent [19]

Coyle et al.

[11] Patent Number: 5,110,963

[45] Date of Patent: May 5, 1992

[54] METHOD FOR MAKING $Mo_4S_4L_6$ (C-2386)

[75] Inventors: Catherine L. Coyle, Mendham, N.J.; Scott A. Farina, Unionville, Pa.; Edward I. Stiefel, Bridgewater, N.J.; Mark A. Greaney, Upper Black Eddy, Pa.

[73] Assignee: Exxon Research & Engineering Company, Florham Park, N.J.

[21] Appl. No.: 708,020

[22] Filed: May 24, 1991

[51] Int. Cl.$^5$ .............................................. C07F 11/00
[52] U.S. Cl. ........................................ 556/61; 556/14; 556/15; 556/28; 556/31; 556/57
[58] Field of Search ....................... 556/57, 61, 14, 15, 556/28, 31

[56] References Cited

U.S. PATENT DOCUMENTS 4,730,064  3/1988  Halbert et al. ........................ 556/15
4,990,271  2/1991  Francis ................................ 252/33.6

OTHER PUBLICATIONS

Kathirgamanathan et al., J. Chem Soc. Chem. Commun., pp. 953–954, 1437–1439 (1985).

Primary Examiner—Jose G. Dees
Assistant Examiner—Porfirio Nazario
Attorney, Agent, or Firm—Joseph J. Dvorak

[57] ABSTRACT

The present invention is predicated on the discovery that Mo(III) containing compounds will react with salts of a 1,1-dithioacid to form $Mo_4S_4L_6$. Accordingly, there is provided a method for preparing compounds of the formula $Mo_4S_4L_6$ wherein L is a 1,1-dithioacid ligand comprising:

contacting a Mo(III) containing compound with the salt of a 1,1-dithioacid at temperatures and for a time sufficient to form the $Mo_4S_4L_6$ compound. Preferably, the Mo(III) containing compound is dissolved in an organic solvent and the solution is heated at temperatures above about 25° C. up to the boiling point of the solvent and, preferably, at temperatures in the range of about 25° C. to about 250° C.

11 Claims, No Drawings

METHOD FOR MAKING MO₄S₄L₆ (C-2386)

FIELD OF THE INVENTION

This invention relates to improvements in the synthesis of $Mo_4S_4L_6$ compounds.

BACKGROUND OF THE INVENTION

Molybdenum compounds having a thiocubane structure are produced by a variety of methods. For example, T. Shibahara et al, *J. Am. Chem. Soc.*, 106, pp. 789–791 (1984) discusses a method for making the $[Mo_4S_4(edta)_2]^{3-}$ ion containing species by reacting a water soluble Mo(V) dimer in HCl. P. Kathirgamanathan et al, *J. Chem. Soc., Chem. Commun.*, pp. 953–954 (1985), describes electrochemically reducing a $Na_2[Mo(V)_2S_2O_2(cysteine)_2] \cdot 3H_2O$ in HCl to form $(Me_4N)_5[Mo_3S_4(NCS)_9]$ and the tetramer $(Me_4N)_7[Mo_4S_4(NCS)_{12}]$. P. Kathirgamanathan et al, *J. Chem. Soc., Chem. Commun.*, pp. 1437–1439 (1985), describes preparing mixtures of $(Me_4N)_5[Mo_3X_4(NCS)_9]$ and $(Me_4N)_7[Mo_4X_4(NCS)_{12}]$ compounds, where X is sulfur or oxygen. More recently, in U.S. Pat. No. 4,990,271 there is described a method for making thiocubane Mo compounds having the formula $Mo_4S_4(ROCS_2)_2$ by reacting molybdenum hexacarbonyl, $Mo(CO)_6$, with a xanthogen disulfide.

Notwithstanding the plethora of methods for preparing molybdenum containing thiocubane type compounds, there remains a need for a preparative method that is more simple and less expensive.

It is, therefore, an object of the present invention to provide an improved method for forming thiocubane Mo compounds of the general formula $Mo_4S_4L_6$, where L is a dithioacid ligand.

SUMMARY OF THE INVENTION

The present invention is predicated on the discovery that Mo(III) containing compounds will react with salts of a 1,1-dithioacid to form $Mo_4S_4L_6$. Accordingly, there is provided a method for preparing compounds of the formula $Mo_4S_4L_6$ wherein L is a 1,1-dithioacid ligand comprising:

contacting a Mo(III) containing compound with the salt of a 1,1-dithioacid at temperatures and for a time sufficient to form the $Mo_4S_4L_6$ compound. Preferably, the Mo(III) containing compound is dissolved in an organic solvent and the solution is heated at temperatures above about 25° C. up to the boiling point of the solvent and, preferably, at temperatures in the range of about 25° C. to about 250° C.

DETAILED DESCRIPTION OF THE INVENTION

According to the method of the present invention, a molybdenum (III) containing compound is employed in forming the thiocubane molybdenum compounds of the present invention. Among the molybdenum (III) containing compounds that are particularly suitable for use in the method of the present invention are halides such as $Mo(III)Cl_3(CH_3CN)_3$, $(NH_4)_2Mo(III)Cl_5(H_2O)$, $(NH_4)_3MoCl_6$, $K_3MoCl_6$, $K_3MoBr_6$, and salts such as $M_3Mo(formate)_6$ where M is an alkali metal or ammonium ion. These molybdenum compounds are prepared by well known synthetic techniques.

In the process of the present invention, the molybdenum compound is dissolved in an organic solvent. Typical useful solvents include alcohols, such as absolute ethanol, nitriles, toluene, $CH_2Cl_2$ and mixtures thereof.

After dissolving the molybdenum (III) compound in a suitable organic solvent, the molybdenum (III) compound is contacted with a salt of 1,1-dithioacid. Typical 1,1-dithioacids include dithiocarbamates, xanthates, thioxanthates, dithiophosphates, dithiophosphinates and mixtures thereof. Typical salts of the 1,1-dithioacids include alkali metal, alkaline earth metals, ammonium and organoammonium compounds. The organo groups in the organoammonium compounds include alkyl, aryl, aralkyl groups having from about 1 to about 30 carbon atoms.

The ratio of the molybdenum (III) compound to the salt of the 1,1-dithioacid will generally be in the range of about 0.01 to 10 and, preferably, in the range of 0.1 to 1.0. The salt of the 1,1-dithioacid and the molybdenum (III) containing compound is contacted at temperatures ranging from above about 25° up to about 250° C. and, generally, up to about the boiling point of the solvent.

Contact times, of course, will depend upon the temperature conditions employed and the ligand chosen and, in general, will range from about 1 hour to about 5 days.

$Mo_4S_4L_6$ compounds made in accordance with the present method are effective as additives in lubricating compositions and contribute excellent antiwear, antioxidant and friction reducing properties therein.

The invention will be more fully understood by reference to the following examples. The examples illustrate modifications of the invention and should not be construed as limiting the scope thereof.

EXAMPLE 1

Synthesis of $Mo_4S_4[(C_2H_5)_2NCS_2]_6$ from $Mo(III)Cl_3(CH_3CN)_3$ (a) Preparation of $Mo(III)Cl_3(CH_3CN)_3$ $MoCl_3(CH_3CN)_3$ was prepared from $MoCl_5$ by the method described by S. Y. Roh and J. W. Bruno in *Inorganic Chemistry*, 25, pp. 3106–3108 (1986).

(b) Preparation of $Mo_4S_4[(C_2H_5)_2NCS_2]_6$

The $Mo(III)Cl_3(CH_3CN)_3$ (1 mole or equivalent) was dissolved in absolute ethanol and refluxed with dry potassium diethyldithiocarbamate (4 moles or equivalent) in absolute ethanol to form $Mo_4S_4[(C_2H_5)_2NCS_2]_6$ which was isolated by filtration in a yield greater than 50%, based on molybdenum.

The composition and structure of the resulting $Mo_4S_4[(C_2H_5)_2NCS_2]_6$ compound was analyzed. The ultraviolet, visible, infrared spectra and electrochemical properties of the resulting compound were found to be the same as that for $Mo_4S_4[(C_2H_5)_2NCS_2]_6$ prepared using $Mo(CO)_6$. Also, the thin layer chromatography retention times were the same as that for $Mo_4S_4[(C_2H_5)_2NCS_2]_6$ prepared from $Mo(CO)_6$.

EXAMPLE 2

Synthesis of $Mo_4S_4[(C_2H_5)_2NCS_2]_6$ from $(NH_4)_2Mo(III)Cl_5(H_2O)$ $Mo(VI)O_3$ was reduced to $(NH_4)_2Ml(III)Cl_5(H_2O)$ by the method described in *Inorg. Synthesis*, 4, p. 97 (1953). The $(NH_4)_2Mo(III)Cl_5(H_2O)$ (231 mg) was then contacted with sodium diethyldithiocarbamate: $Na[(C_2H_5)_2NCS_2] \cdot 3H_2O$ (901 mg or 4 mmol) in degassed absolute ethanol (50 ml) and the entire mixture was refluxed at 100° C. for 18 hours. The ethanol was then evaporated off and the resulting residue was extracted with methylene chloride (15 ml). $Mo_4S_4[(C_2H_5)_2NCS_2]_6$ was recovered in approximately a 25% yield based on molybdenum from a 3 cm × 6 cm silica gel chromatography column using $CH_2Cl_2$ as the eluent.

EXAMPLE 3

Synthesis of $Mo_4S_4[(C_8H_{17})_2NCS_2]_6$ from $Mo(III)Cl_3(CH_3CN)_3$ $Mo(V)Cl_5$ was converted to $Mo(III)Cl_3(CH_3CN)_3$ by the procedure outlined in Example 1. The Mo-$(III)Cl_3(CH_3CN)_3$ (250 mg 0.77 mmol) was dissolved in degassed, anhydrous ethanol (20 ml). In a separate flask, potassium tertiary butoxide (346 mg or 3.08 mmols), dioctylamine (774 mg or 3.08 mmoles) and carbon disulfide ($CS_2$) (234 mg or 3.08 mmoles) were added to the anhydrous ethanol (20 ml) and degassed. This degassed solution was added to the molybdenum/ethanol solution and the entire mixture was refluxed for several days. Afterwards, the mixture was filtered in order to remove the precipitate that formed and the resulting filtrate was evacuated to dryness. The dried material was dissolved in $CH_2Cl_2$ and acetonitrile was added to isolate $Mo_4S_4[(C_8H_{17})_2NCS_2]_6$ as a dark purple oil. The oil was dried in a vacuum oven at 105° C. for 1 hour. The yield was 53% based on molybdenum.

What is claimed is:

1. A method for preparing a compound of the formula $Mo_4S_4L_6$ wherein L is a 1,1-dithioacid, comprising:

contacting a Mo(III) containing compound with a salt of a 1,1-dithioacid at temperatures and for a time sufficient to form a $Mo_4S_4L_6$ compound.

2. The method of claim 1 wherein the contacting is conducted in a solvent.

3. The method of claim 2 wherein the solvent is selected from the group consisting of alcohols, nitriles, $CH_2Cl_2$, toluene and mixtures thereof.

4. The method of claim 3 wherein the contacting is conducted at temperatures ranging from 25° C. to 250° C.

5. The method of claim 4 wherein the Mo(III) containing compound is a Mo(III) halide.

6. The method of claim 5 wherein the salt of the 1,1-dithioacid is selected from alkali, alkaline earth, ammonium and organoammonium salts.

7. The method of claim 6 wherein the Mo(III) halide is selected from $Mo(III)Cl_3(CH_3CN)_3$ and $(NH_2)_2Mo(III)Cl_5(H_2O)$.

8. The method of claim 7 wherein the dithioacid is selected from dithiocarbamates, xanthates, thioxanthates, dithiophosphates, dithiophosphinates and mixtures thereof.

9. The method of claim 8 wherein the contacting is conducted for 1 hour to 5 days.

10. A method for preparing a compound of the formula $Mo_4S_4L_6$ wherein L is a 1,1-dithioacid, comprising:

contacting a Mo(III) halide and a salt of a 1,1-dithioacid in an organic solvent at temperatures in the range of from about 25° C. to 250° C. for a time sufficient to form the $Mo_4S_4L_6$ compound, the salt of the 1,1-dithioacid being selected from alkali, alkaline earth, ammonium and organoammonium salts of 1,1-dithioacids, the 1,1-dithioacid being selected from the group consisting of dithiocarbamates, thioxanthates, xanthates, dithiophosphates, dithiophosphinates and mixtures thereof; and the organic solvent selected from the group consisting of alcohols, nitriles, toluene, $CH_2Cl_2$ and mixtures thereof.

11. The method of claim 10 wherein the organic solvent is absolute ethanol and the salt is an alkali metal salt.

* * * * *